United States Patent [19]

Mazor

[11] Patent Number: 4,561,432

[45] Date of Patent: Dec. 31, 1985

[54] FRACTURED FEMUR FIXATION SYSTEM

[75] Inventor: Boris B. Mazor, Beverly Hills, Calif.

[73] Assignee: Floyd A. Coard, M.D., Los Angles, Calif.

[21] Appl. No.: 532,361

[22] Filed: Sep. 15, 1983

[51] Int. Cl.⁴ .............................................. A61F 5/04
[52] U.S. Cl. ........................... 128/92 BA; 128/92 EC
[58] Field of Search ............ 128/92 BA, 92 B, 92 BB, 128/92 EB, 92 EC

[56] References Cited

U.S. PATENT DOCUMENTS

| | | | |
|---|---|---|---|
| 2,235,419 | 3/1941 | Callahan et al. | 128/92 BA |
| 2,239,088 | 4/1941 | Ettinger | 128/92 BA |
| 2,537,070 | 12/1948 | Longfellow | 128/92 |
| 2,602,445 | 7/1952 | Gallant et al. | 128/92 BA |
| 2,702,031 | 2/1955 | Wenger | 128/92 R |
| 2,716,406 | 8/1955 | Reymann et al. | 128/92 BA |
| 2,761,444 | 9/1956 | Luck | 128/92 BA |
| 2,937,642 | 5/1960 | Lange et al. | 128/92 BA |
| 3,076,453 | 2/1963 | Fronzo | 128/92 BA |
| 3,216,414 | 11/1965 | Street | 128/92 R |
| 3,561,437 | 3/1968 | Orlich | 128/92 |
| 3,892,233 | 7/1975 | Vestby | 128/92 BA |
| 4,103,683 | 8/1978 | Neufeld | 128/92 B |

FOREIGN PATENT DOCUMENTS

| | | | |
|---|---|---|---|
| 196243 | 8/1967 | U.S.S.R. | 128/92 BA |
| 862940 | 9/1981 | U.S.S.R. | 128/92 BA |
| 921547 | 4/1982 | U.S.S.R. | 128/92 BA |
| 984469 | 1/1983 | U.S.S.R. | 128/92 BA |

*Primary Examiner*—Gene Mancene
*Assistant Examiner*—C. W. Shedd
*Attorney, Agent, or Firm*—Jack C. Munro

[57] ABSTRACT

Apparatus in the form of a system for fixing fractures of the femur which includes a nail to be inserted in the proximal extremity of the femur. The fore end of the nail includes a plurality of prongs which tend to spread apart as the nail is inserted. A guide rod is initially inserted into the femur and is used as a guide for the nail during its insertion. A locating bracket is utilized to facilitate inserting of the guide rod. The nail is connected to a driving handle which is then manually operated to insert the nail in its correct position. A force applying device, which includes a turnbuckle assembly, is to be connected to the nail to facilitate removal of the nail after the fracture in the femur has healed.

10 Claims, 11 Drawing Figures

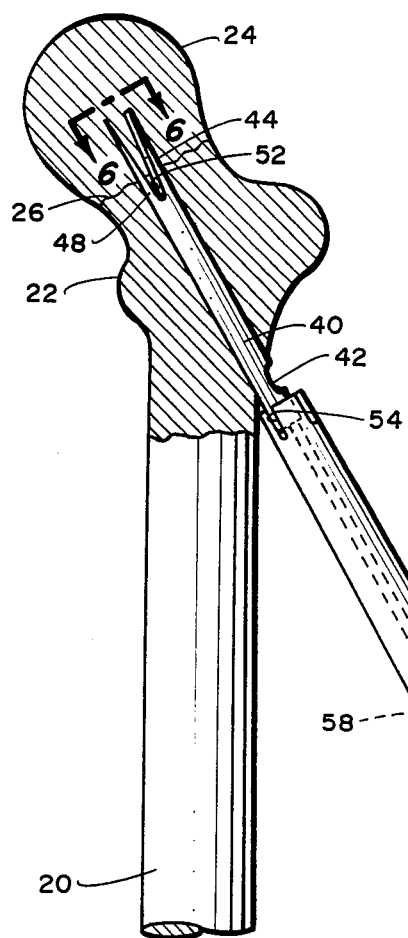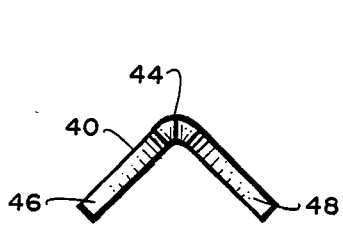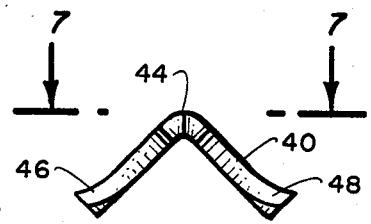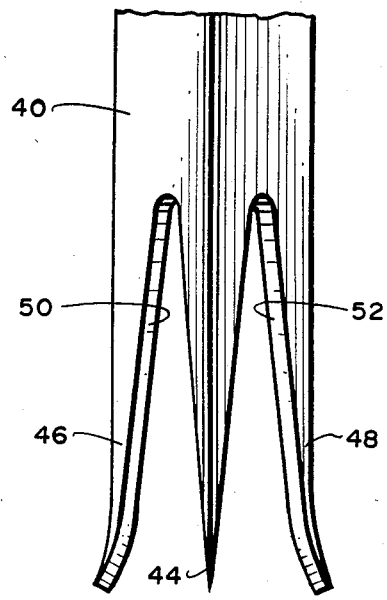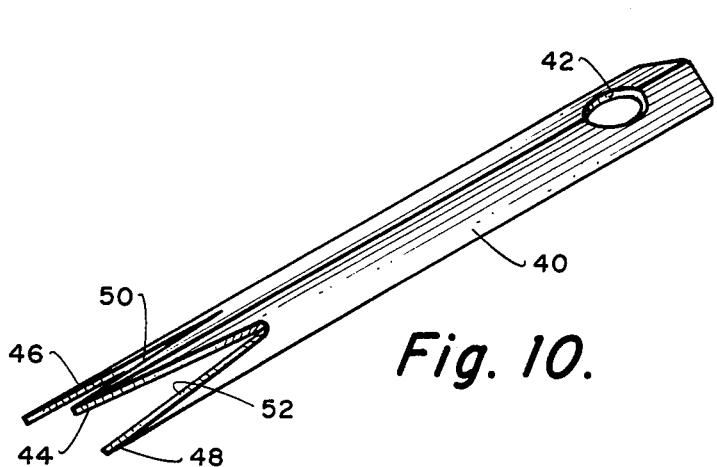

FRACTURED FEMUR FIXATION SYSTEM

BACKGROUND OF THE INVENTION

The field of this invention relates to an apparatus for supporting and maintaining together fractured bone sections of the femur in the normal position to assist in proper healing.

The femur, at the hip, terminates at a femoral head. Connecting the femoral head to the main portion of the femur is a femoral neck. The head constitutes an enlarged ball shaped bone tissue, while the femoral neck is a smaller diametered cylindrical shaped bone tissue. The femoral head is composed of spongy tissue while the femoral neck is composed of hard bone tissue similar to the main body of the femur.

Fractures of the femur, particularly across the femoral neck, are rather common. It was determined quite early that the setting of such fractures by using casts, was not likely to be very successful, due to movement of the hip joint. It was quickly determined that some means would be required for internal fixation of the proximal end of the femur.

Initially attempts were made at internal fixation through the use of either a round or a polygonal shaped nail. However, this type of nail was quickly abandoned because it brought about only partial and temporary fixation. Then in the late 20's, it was discovered that good fixation could be achieved by using a flanged nail. This type of nail came to be known as the Smith-Petersen Nail, named after its inventor.

Soon after the development of the Smith-Petersen nail, it was determined that even a better fixation of the fracture could be achieved by attaching a plate to the lateral side of the shaft of the femur. One good use of such a plate would be to prevent the nail in time from working itself out of position. Usually such nails are required to remain in position for extended periods of time, such as three to six months. However, usage of such a plate has several disadvantages such as destroying additional bone tissue in attaching of the plate to the femur, significantly increasing the equipment which the patient must tolerate over an extended length of time, significantly complicates the attachment at the back end of the nail, and such plates do not allow the patient to be mobilized as soon as the patient should. The results of a patient remaining too long in a sedimentary position are well known for those in the medial profession. Sedimentation is particularily hazardous for geriatrics, the group of persons most likely to incur fractures of the femur, because geriatrics readily contract pneumonia, respiratory problems, heart problems, ulcers, or generalized weakness when subjected to inactivity.

Although the Smith-Petersen nail significantly enhanced the fixation of the femur, a high percent of postoperative complications still arise. The most important complications are:

1. The fracture will not unite in about ten percent of the cases, and
2. The femoral head becomes necrotic and fragmentates (referred to as capital necrosis) in about thirty to forty percent of the cases.

It is now generally assumed that capital (necrosis) is due to vascular injuries. As the tip of the Smith-Petersen nail penetrates the femoral head, a significant amount of area of the tissue within the femoral head is destroyed. It is believed that this destroying of the tissue produces the capital necrosis since the nail causes significant damage to the blood supply to the femoral head. When capital necrosis does occur, it is necessary to re-operate on the patient, remove the femoral head, and insert a metallic prosthesis.

The problem with the fracture not uniting, is believed to be due to poor fixation of the femoral head to the femur. This is an indication that the Smith-Petersen nail is not entirely satisfactory.

SUMMARY OF THE INVENTION

One of the objectives of the present invention is to construct a hip nail which is designed to minimize vascular injury within the femoral head while also achieving improved fixation without the use of any additional structures, such as a plate attached to the lateral side of the femur.

The system of the present invention provides for utilizing a locating bracket which is to be placed against the lateral surface of the femur after the incision is made through the skin at the appropriate location. The locating bracket includes an opening assembly through which is to be inserted a sharp pointed guide rod. The guide rod is to be guidingly inserted by the locating bracket through the femur, through the femoral neck and into the femoral head. The exact angle of penetration is to be observed by the use of X-rays. After the guide rod has be properly inserted, the locating bracket is removed and the hip nail is then placed against the guide rod ready to begin insertion through the femur and into the femoral head. The driving handle is connected to the aft end of the hip nail with the guide rod passing through an opening in the driving handle. The driving handle is then manually operated to drive the hip nail into the femoral head with the hip nail moving along the guide rod. Upon the hip nail achieving the desired depth, which is again determined through the use of X-rays, the guide rod is removed and the driving handle is disengaged from the hip nail. Several months later when it is necessary to remove the hip nail, a turnbuckle and a manually operated actuator assembly is to connect to the aft end of the hip nail for slow steady removal.

BRIEF DESCRIPTION OF THE DRAWINGS

FIG. 5 is a view similar to FIG. 1 but showing the hip nail in the completely installed position;

FIG. 6 is an end view of the front end of the hip nail, exaggerated for illustrative purposes showing the outward expanding of the prongs when the hip nail is installed;

FIG. 6a is a view similar to FIG. 6 depicting the prongs of the hip nail prior to installation within the femur;

FIG. 7 is a fragmentary elevational view of the fore end of the hip nail taken along line 7—7 of FIG. 6;

FIG. 10 is an isometric view of the hip nail itself.

DETAILED DESCRIPTION OF THE SHOWN EMBODIMENT

Figures 1, 2, 3, 4:
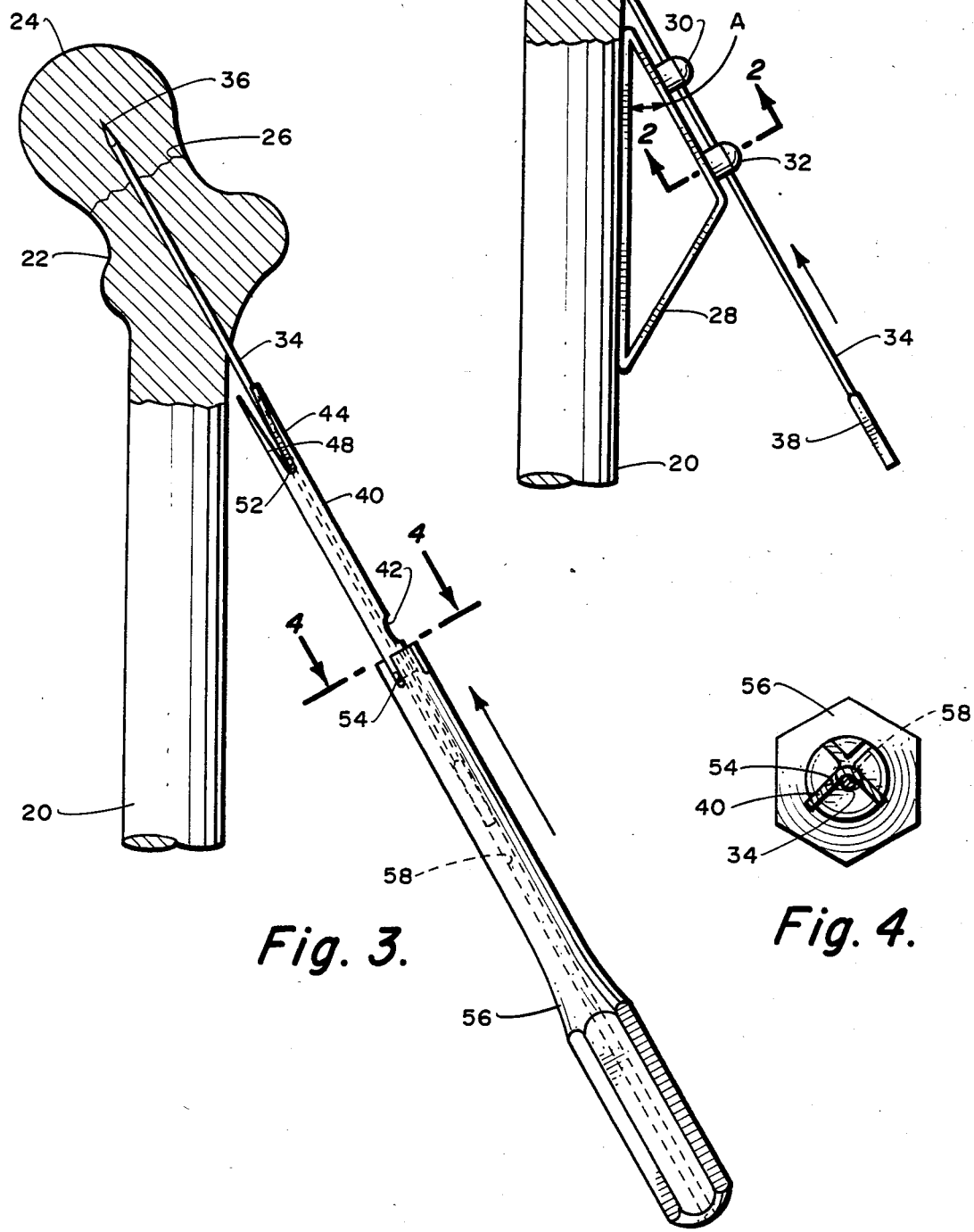
FIG. 1 is a schematic fragmentary elevational view depicting a fractured femur to which the system of the present invention is to be applied showing the guide rod being inserted to its proper location.
FIG. 2 is a cross sectional view through the guide rod and the locating bracket taken along line 2—2 of FIG. 1.
FIG. 3 is a view similar to FIG. 1 showing the hip nail connected to the driving with the hip nail in position to be inserted through the femur.
FIG. 4 is a cross sectional view through the hip nail showing the connection of the hip nail to the driving handle.

Referring to the drawings there is depicted within FIGS. 1, 3, 5, 8 and 9, the general appearance of the femur bone 20, which has a femoral neck 22 and a femoral head 24. Within FIGS. 1, 3 and 5 there is depicted a fracture 26 in the area of the neck 22. Within FIGS. 8 and 9 the fracture has healed.

After the physician has made an incision exposing the femur bone 20, the physician locates locating bracket 28 against the lateral surface of the femur bone 20 as shown in FIG. 1 of the drawings. The locating bracket 28 is formed of sheet material in the shape of a triangle. On one side of bracket 28 there are located a pair of spaced-apart protuberances 30 and 32. The protuberances 30 and 32 each includes small hole (not shown) which are aligned. Only hole 33 in protuberance 32 is shown. A guide rod 34 is to be located through the aligned openings within the protuberances 30 and 32 as is shown in FIG. 1 of the drawings.

The angle A of the bracket 28 has been preselected (approximately 45°) so that with the bracket 28 located in proper position against the femur, the guide rod 34 will be directed through the femur 20 and through the center of the neck 22 and the head 24. The guide rod 34 has a sharp point 36 at its front end and a flattened grasping surface 38 at its back end. Guide rod 34 will normally be constructed of stainless steel and will be of a very small diameter, such as 1/16 or ⅛ of an inch. The physician is to grasp at the flattened area 38 and maneuver the guide rod 36 to the position shown in FIG. 1 through the use of an X-ray machine (not shown).

The physician now removes the locating bracket 28 from its position against the femur and then completely disengages the bracket 28 from the back end of the guide rod 34. The back end of the guide rod 34 will merely slip through the aligned openings, only opening 33 being shown, formed within the protuberances 30 and 32.

The physician then is to utilize the hip nail 40 which is to be constructed of a stainless steel and will be of a length of between 100 to 120 millimeters. The hip nail 40 in transverse cross-section forms a right angle. Adjacent the aft end of the hip nail 40 is a opening 42. The function of the opening 42 will be explained further on in this specification.

The fore end of the hip nail 40 is formed into a plurality of prongs comprising a center prong 44 which is located between a pair of side prongs 46 and 48. It is to be noted that the tip of each of the prongs 44, 46 and 48 is sharpened. The tip of prong 44 is noted to be straight, while the tips of the prongs 46 and 48 are shown particularly in FIG. 7 to be slightly outwardly flared. This is so that as the nail 40 is inserted into its proper position within the femur, the prongs 46 and 48 slightly deflect in an outward direction away from the center prong 44. This outward deflection is shown in exaggeration in FIG. 6. This outward deflection is desirable as there will be a natural tendency for the prongs 46 and 48 to return to their natural position but are prevented from so doing by the portion of the femoral head 24 being held there between. This creates a certain holding force that grasps tightly on the femoral head 24 and functions to prevent accidental withdrawal of the nail 40 after it is located in the desired position. This deflection occurs not only due to the flaring of prongs 46 and 48 but also by reason of the length of the prongs 46 and 48 being substantially equal in length to prong 44. The length of prongs 46 and 48 must be great enough to permit this deflection.

It is to be noted that separating the prongs 44 and 46 is a deep groove 50. A similar deep groove 52 separates prongs 44 and 48. The function of the grooves 50 and 52 is to minimize the amount of material of the nail 40 that penetrates the femoral head 24. The reason for this is to minimize the destruction of the tissue to the femoral head 24 and thereby decrease the possibility of necrosis in respect to the femoral head 24. The amount of tissue of the head 24 which is destroyed or damaged is actually quite small when compared to the overall quality of tissue of the head 24.

Nail 40 must be inserted through the femur and into the femoral head 24 with a substantial amount of force. In order to achieve this, the aft end of the nail 40 is slipped into a slot 54 of a driving handle 56. Slot 56 functions to locate nail 40 in tight connection to the handle 56. Also located through the handle 56 is elongated through opening 58. The guide rod 34 is to be located through the opening 58.

Nail 40, with the handle 56 attached, is to be located against the guide rod 34 so that the guide rod 34 is against the inside surface of the nail 48 and in substantially alignment with the center prong 44. The guide rod 34 partially extends in the opening 58. The physician then begins to strike the back end of the handle 56 like with the palm of his hand which will then cause the nail 40 to be driven through the femur 20 and finally into the femoral head 24. The exact depth of driving of the nail 40 is to be controlled through the use of an X-ray machine.

After the nail 40 has been completely inserted, the physician then grasps the flattened area 38 of the rod 34 and then pulls such from the femoral head 24 and the femur 20 and out through the opening 58 to be completely separated from the handle 56. The physician then separates the handle 56 from the nail 40. The nail 40 is now established in its proper position and should remain that way for approximately six months. The incision that was made during performing the operation is now sealed.

After the fracture has healed, the physician then reenters to the area of the nail 40 and locates a hook 60 of a turnbuckle assembly 62 in contact with the opening 42. The hook 60 threadably engages with the frame 64 of the turnbuckle assembly 62. A second hook 66 also threadably engages with the frame 64. The hook 66 connects with member 68 mounted on threaded rod 70. Threaded rod 70 is threadingly movable within a housing 72. The outer end of the threaded rod 70 is attached to a handle 74.

Figures 8, 9:
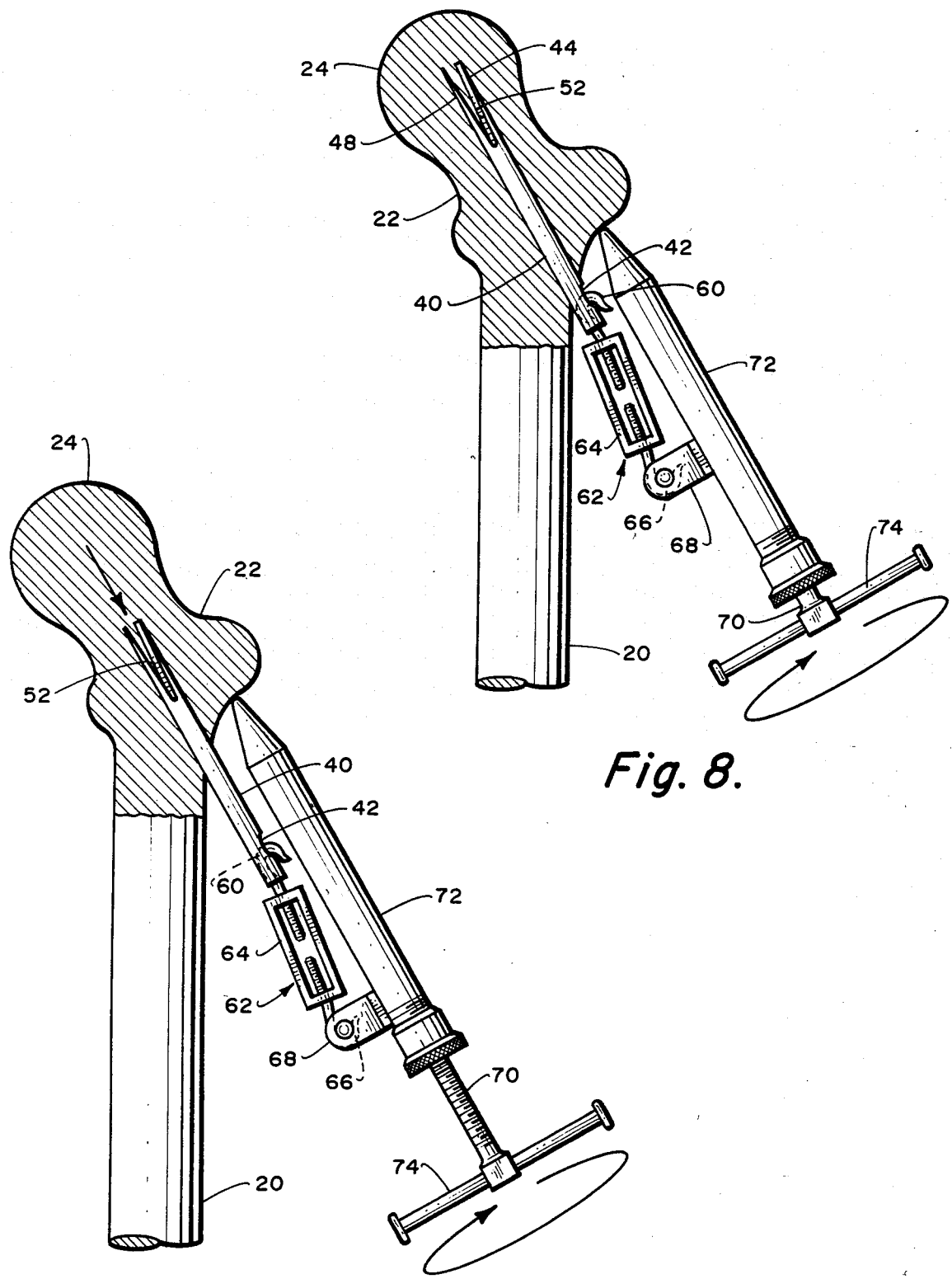
FIG. 8 is a view similar to FIG. 1 showing the structure which is to be utilized to affect removal of the hip nail with the structure at the position beginning to remove the hip nail.
FIG. 9 is a view similar to FIG. 8 showing the hip nail just removed from the femur.

The tip of the housing 72 is to be located as shown in FIG. 8 of the drawings in contact with the femur 20. The member 68 is prelocated as close as possible to the tip of the housing 72. The turnbuckle assembly 62 is preadjusted so that the hook 66 will engage with the member 68 and also the hook 60 will be located with the opening 42.

The physician then begins to turn threaded rod 70 by handle 74. As a result there is a withdrawing force slowly exerted against the nail 40. The physician continues to turn the handle 74 until the nail 40 is completely withdrawn from the femur 20 as is shown within FIG. 9 of the drawings.

The physician then closes the wound and the hole that remains within the femur 20 and the femoral head 24 due to withdrawing of the nail 40 will eventually close up.

What is claimed is:

1. A fractured femur fixation system for assisting in healing of the femur, said system comprising:
a nail adapted to be forced into the proximal extremity of the femur, said nail being formed of rigid sheet material, said nail being elongated terminating in a fore end and an aft end, said nail in transverse cross-section having an angular configuration, said fore end being formed into a plurality of prongs with there being a pair of side prongs and a center prong located there between, said center prong having a sharpened straight tip, each said side prong having a sharpened outwardly flared tip, the length of said side prongs being substantially equal to the length of said center prong, whereby as said nail is forced into the femur the said tips of said side prongs slightly spread apart which creates a holding force tending to retain said nail in its established position, whereby said system also includes means for nail placement and means for nail extraction.

2. The system as defined in claim 1 wherein said means for nail placement includes:
a guide rod to be initially inserted in said femur prior to inserting of said nail, said nail to be abuttingly located against said guide rod during insertion of said nail.

3. The system as defined in claim 2 wherein said means for nail placement further includes:
a locating bracket to be positioned against the femur prior to insertion of said guide rod, connecting means mounted on said locating bracket, said guide rod to connect with said connecting means to facilitate correct insertion of said guide rod.

4. The system as defined in claim 3 wherein said means for nail placement further includes:
a driving handle, said aft end of said nail to connect with said driving handle, said driving handle to be manally operated to forcibly insert said nail into the femur.

5. The system as defined in claim 4 wherein said means for nail extraction comprises:
said nail includes an aperture, said aperture being located directly adjacent to said aft end, said aperture to facilitate connection with said means for nail extraction.

6. The system as defined in claim 5 wherein said means for nail extraction further comprises:
connection means for connection with said aperture of said nail, said connection means including a force applying structure to be manually operated to effect removal of said nail.

7. The system as defined in claim 1 wherein said means for nail placement further includes:
a driving handle, said aft end of said nail to connect with said driving handle, said driving handle to be manually operated to forcibly insert said nail into the femur.

8. The system is defined in claim 1 wherein said means for nail extraction comprises:
said nail includes an aperture, said aperture being located directly adjacent said aft end, said aperture to facilitate connection with said means for nail extraction.

9. The system as defined in claim 8 wherein said means for nail extraction further comprises:
connection means for connection with said aperture of said nail, said connection means including a force applying structure to be manually operated to effect removal of said nail.

10. A fractured femur fixation system for assisting in healing of the femur, said system comprising:
a nail adapted to be forced into the proximal extremity of the femur, said nail being formed of rigid sheet material, said nail being elongated terminating in a fore end and an aft end, said nail in transverse cross-section having an angular configuration, said fore end being formed into a plurality of prongs with there being a pair of side prongs and a center prong located there between, said center prong having a sharpened straight tip, each said side prong having a sharpened outwardly flared tip, whereby as said nail is forced into the femur the said tips of said side prongs slightly spread apart which creates a holding force tending to retain said nail in its established position, whereby said system also includes means for nail placement and means for nail extraction; and
said nail includes an aperture, said aperture being located directly adjacent said aft end, said aperture to facilitate connection with said means for nail extraction, said means for nail extraction including a force applying structure to be manually operated to effect removal of said nail,
said means for nail extraction comprising a turnbuckle assembly.

* * * * *